United States Patent
Vilser et al.

(10) Patent No.: US 12,016,630 B2
(45) Date of Patent: Jun. 25, 2024

(54) METHOD AND DEVICE FOR EXAMINING THE NEUROVASCULAR COUPLING AT THE EYE OF A PATIENT

(71) Applicant: Imedos Systems GmbH, Jena (DE)

(72) Inventors: Walthard Vilser, Rudolstadt (DE); Martin Skorsetz, Jena (DE); Thomas Riemer, Jena (DE)

(73) Assignee: IMEDOS SYSTEMS GMBH, Jena (DE)

( * ) Notice: Subject to any disclaimer, the term of this patent is extended or adjusted under 35 U.S.C. 154(b) by 908 days.

(21) Appl. No.: 17/042,836

(22) PCT Filed: Mar. 29, 2019

(86) PCT No.: PCT/DE2019/100295
§ 371 (c)(1),
(2) Date: Sep. 28, 2020

(87) PCT Pub. No.: WO2019/185096
PCT Pub. Date: Oct. 3, 2019

(65) Prior Publication Data
US 2021/0113080 A1     Apr. 22, 2021

(30) Foreign Application Priority Data
Mar. 29, 2018   (DE) ..................... 10 2018 107 623.1

(51) Int. Cl.
*A61B 3/12*  (2006.01)
*A61B 3/00*  (2006.01)
*A61B 3/10*  (2006.01)

(52) U.S. Cl.
CPC .......... *A61B 3/1233* (2013.01); *A61B 3/0008* (2013.01); *A61B 3/102* (2013.01); *A61B 3/1241* (2013.01)

(58) Field of Classification Search
CPC ..... A61B 3/1233; A61B 3/0008; A61B 3/102; A61B 3/1241
(Continued)

(56) References Cited

U.S. PATENT DOCUMENTS

| | | |
|---|---|---|
| 8,658,989 B2 | 2/2014 | Ikami et al. |
| 8,791,290 B2 | 7/2014 | Hasegawa et al. |

(Continued)

FOREIGN PATENT DOCUMENTS

| | | |
|---|---|---|
| DE | 10357734 B4 | 10/2009 |
| EP | 1906811 B1 | 4/2016 |

(Continued)

OTHER PUBLICATIONS

International Search Report from PCT/DE2019/100295, filed Mar. 29, 2019, mailed Jun. 5, 2019.

(Continued)

*Primary Examiner* — Joseph P Martinez
*Assistant Examiner* — Grant A Gagnon
(74) *Attorney, Agent, or Firm* — Patentbar International

(57) ABSTRACT

A method and a device for examining the neurovascular coupling at the eye (A) of a patient, wherein an imaging method is used to record an image sequence of images of the fundus of the eye (A), preferably over a baseline phase (BP), a stimulation phase (SP) in which the fundus is stimulated with a flickering light, and a posterior phase (NP). Signals, in particular an averaged quotient signal (Q(t)) representing a vessel response of the vessels of the capillary vessel region to the stimulation, are derived from the image sequence for at least one capillary vessel region of the fundus. The absolute or percentage maximum change ($Q_{max}$) of the averaged quotient signal (Q(t)) is then used as an evaluation criterion for the neurovascular coupling.

18 Claims, 4 Drawing Sheets

(58) Field of Classification Search
USPC .......................................................... 351/206
See application file for complete search history.

(56) References Cited

U.S. PATENT DOCUMENTS 9,174,089 B2    11/2015  Shiga et al.
10,368,734 B2 *  8/2019  Durbin ................. A61B 3/0025

FOREIGN PATENT DOCUMENTS

| JP | 2008208036 A  | 9/2008  |
| JP | 2008295971 A  | 12/2008 |
| JP |    6606186 B2 | 6/2018  |
| WO | 2005/079658 A2 | 9/2005 |
| WO | 2005/094668 A1 | 10/2005 |

OTHER PUBLICATIONS

Garhofer, G., et al., Use of the retinal vessel analyzer in ocular blood flow research, Acta Ophthalmologica, 2010, pp. 717-722, v. 88.
Vilser, W. et al, Quantitative assessment of optic nerve head pallor, Physiological Measurement 29 (2008), pp. 451-457.

* cited by examiner

METHOD AND DEVICE FOR EXAMINING THE NEUROVASCULAR COUPLING AT THE EYE OF A PATIENT

RELATED APPLICATIONS

This Application is a U.S. National Stage Under 35 USC § 371 of International Application PCT/DE2019/100295, filed on Mar. 29, 2019, which in turn claims priority to German Patent Application DE 10 2018 107 623.1, filed Mar. 29, 2018, both of which are incorporated herein by reference in their entirety.

FIELD OF THE INVENTION

The area of application of the invention relates to the entire field of vascular medicine, e.g. in ophthalmology, neurology, cardiology, nephrology, diabetology, and hypertensiology.

BACKGROUND OF THE INVENTION

It is known from studies that microvascular changes are frequently of a systemic nature, i.e. they occur similarly in the vessels, in particular the microcirculation vessels of all organs in the human and animal body, and, depending on the organ, lead to different manifestations of cardiovascular conditions, such as atherosclerosis, arteriosclerosis, cardiac insufficiency, renal insufficiency, eye conditions, e.g. retinopathies and glaucoma, cerebrovascular conditions, e.g. vascular dementia, and may ultimately trigger or are predictors of cardiovascular events, such as myocardial infarction and stroke. As a unique optical window to microcirculation, the eye allows the retinal vessels to be examined as a mirror image of the vessels in inaccessible regions of the other organs in the body. The field of application of the invention is to examine vascular endothelial function in human vessels and neurovascular coupling.

In ophthalmology, imaging methods and devices are currently used, above all, in clinical examinations of structural or morphological changes at the eye, in particular the ocular fundus (in the retina). These include conventional fundus cameras, OCT, laser scanners, systems with adaptive optics and other vascular examinations by means of static vessel analysis, e.g. using the VesselMap available from Imedos, have begun to penetrate everyday clinical practice in microvascular risk stratification and therapy monitoring.

So far, functional examination of the retinal vessels has been applied predominantly in research, e.g. devices and methods for measuring blood velocity and vessel diameters on the basis of indicators as well as systems for dynamic vessel analysis. The fields of application of the Doppler- or OCT-based systems provide statements that describe the vascular or flow state and thus are of little importance for vascular diagnostics outside ophthalmology and are unable to capture the function of vascular regulation.

Dynamic vessel analysis enables the examination of various autoregulation mechanisms on the basis of continuous measurements of the vessel diameters over time and along the location of the so-called large arteries and veins of microcirculation. The retinal vessels are stimulated or provoked during the recording of the vessels and respond accordingly by constriction or dilation, which describes the vessel response of the retinal autoregulation mechanisms addressed by the respective type of stimulation or provocation and their functionality.

Such stimulation or provocation methods allow examination of various autoregulation mechanisms of microcirculation. One of said autoregulation mechanisms is flow-induced autoregulation.

The dynamic vessel analysis system constituting the prior art is the Dynamic Vessel Analyzer (DVA) from Imedos (Garhofer, G., Bek, T., Böhm, A. G., Gherghel, D., Grunwald, J., Jeppesen, P., Kergoat, H., Kotliar, K., Lanzl, I., Lovasik, J. V., Nagel, E., Vilser, W., Orgul, S., Schmetterer, L.: "Use of the retinal vessel analyzer in ocular blood flow research". Acta Ophthalmologica 2010: 88: pages 717-722.) The standard provocation used in the DVA is flickering light, which operates in a frequency range of 12.5 Hz and uses an optical shutter to interrupt the green measuring light in a flickering manner for 20 s. This operation is repeated three times and the vessel responses are then superimposed upon each other for averaging and evaluated with respect to the maximum dilation and subsequent constriction.

These measurements are restricted in the DVA to the large vessels of microcirculation between 60 and 300 μm.

The parameters of the evaluation (maximum dilation) as well as other derivable parameters, are interpreted as biomarkers for the function diagnostics examination of the microvascular endothelial function. Erroneously, some authors also refer to and interpret the parameters of the vessel response as parameters of neurovascular coupling. However, there is evidence that, while neurovascular coupling may represent the initial stimulus, thus influencing vessel response, the vessel response of the large vessels describes the function of the endothelial function.

Further, WO 2005/094668 A1 describes a device for photometrically measuring the vessel diameters of smaller vessels. The disclosed technical solution allows the measurement of vessel diameters in the area of the arterioles and venules, provided the vessels in the fundus image are selectable as vessels. For this purpose, two different spectral ranges and a color camera are used. This considerably increases the retina's exposure to light. However, another substantial disadvantage of the disclosed solutions also consists in the fixed illumination-side arrangement of a light modulator in the joint illumination-side beam path, which likewise only allows flexible temporal modulation and substantially restricts the range of applications and adaptivity, ultimately having the same disadvantages as the DVA, except for the advantage of being able to also perform measurements on small retinal vessels that are, however, significantly larger than capillaries.

Another technical solution for measuring capillary "perfusion" is described in the article by Vilser et al. from 2008 (Vilser, W., Nagel, E., Seifert, B. U., Riemer, T., Weisensee, J., Hammer, M: "Quantitative assessment of optic nerve head pallor". Physiological Measurement 29 (2008), pages 451-457). Using a dual bandpass filter in the illumination beam path of a conventional retinal camera, two spectral regions in the red and green spectral ranges of the white illumination light are selected and assigned to the red and green color channels of a 3-chip color CCD camera such that both selected illumination-side spectral ranges of the measuring light are received separately by the two assigned red and green color channels of the CCD camera. Based on the detected intensity values of both color channels (red and green) by pixels which can be assigned to the same fundus location, quotients are formed and in turn assigned to the fundus location. The resulting quotient image is then evaluated with respect to the capillary perfusion on the optic nerve head.

Although this method does not allow representation of the perfusion of the optic nerve head, if perfusion is understood to mean the capillary blood flow, but it provides a measure of the blood volume and, thus, of the capillary vessel diameter and the capillarization of the examined tissue volumes. The disadvantage of this method is that, in contrast to the description in the aforementioned paper, it cannot provide functional statements about the regulation of capillary perfusion.

A first major drawback of the prior art is the lack of possibilities to examine neurovascular coupling in the retina. Methods for examining neurovascular coupling in the brain are purely experimental, invasive, very costly and not suitable for clinical use. Neurovascular coupling plays a key role for retinal and cerebral blood flow as well as for various diseases.

A further disadvantage of the prior art is that the results of studies on vascular endothelial function are highly scattered and thus the correlation between endothelial dysfunction and cardiovascular risk factors, events and diseases is unclear, which makes clinical use for the individual assessment of endothelial function and the diagnosis of endothelial dysfunction faulty and unreliable.

It is the object of the invention to find a method for the non-invasive, non-contact and simple examination of neurovascular coupling in the retina and on the optic nerve head that is suitable for clinical non-invasive use.

SUMMARY OF THE INVENTION

A further object of the invention is to find a device to carry out the method.

With respect to a method of examining the neurovascular coupling at the eye of a patient, the object is achieved by a first method in which an imaging method is used to create and record an image sequence of images of the fundus of the eye while the fundus is stimulated with a flickering light, wherein signals are derived from the images of the image sequence for at least one capillary vessel region of the fundus, which represent capillary vessel responses of the capillaries of the capillary vessel region to the stimulation with the flickering light and whose maximum absolute or percentage change is determined and used as an evaluation criterion for the neurovascular coupling.

Moreover, signals are advantageously derived from the images of the image sequence also for at least one vessel section of arterial or venous vessels of the fundus, which signals represent arterial or venous vessel responses to the stimulation and their maximum absolute or percentage change is determined, which represents an evaluation criterion for the endothelial function.

In this context, it is irrelevant whether the basic imaging technology is realized by conventional fundus camera technology, OCT technology, adaptive optics technology or scanning technology, as long as an image sequence with sufficient temporal resolution is generated. Furthermore, it is irrelevant whether the signals derived from the image reflect e.g. the vessel diameter, blood volume, blood velocity, blood flow, capillary density or other parameters, as long as these signals describe a reaction of the retinal vessels, including the capillaries, to the stimulation (vessel response).

Using the maximum absolute or percentage change in capillary vessel responses as a reference value for the maximum absolute or percentage change in arterial and/or venous vessel responses, e.g. by calculating a quotient, an evaluation criterion is advantageously obtained for an evaluation of vascular endothelial function free from the influence of neurovascular coupling.

The signals describing the vessel responses may represent intensities, vessel diameters, blood volume values, quotient signals from different spectral ranges, blood flow values, vessel densities or blood velocity values of the capillary or larger arterial or venous vessels.

The recording of an image sequence of images of the fundus of the eye is advantageously carried out over a baseline phase, a stimulation phase in which the fundus is stimulated with the flickering light, and a posterior phase (NP).

Advantageously, the method integrates the examination of endothelial function in the large retinal vessels, using the vessel response describing the neurovascular coupling as a reference for the evaluation of the vessel response describing the endothelial function. It is irrelevant how said reference is implemented. An example is the formation of a quotient from the percentage maximum dilation of the large vessels and the percentage maximum change of the vessel response of the neurovascular coupling. Just the information about the strength of the neurovascular coupling is already sufficient to evaluate the examined vascular endothelial function. Thus, the influence of neuronal coupling on the examination of the vascular endothelial function can be eliminated, thereby avoiding errors in the assessment of endothelial function and significantly improving diagnostic reliability.

With respect to a method for examining neurovascular coupling at the eye of a patient, the object is also achieved by a second method, in which an imaging method is used to record an image sequence of images of the fundus of the eye over a baseline phase, a stimulation phase in which the fundus is stimulated with a flickering light, and a posterior phase (NP), wherein the fundus is illuminated with measuring light of two different spectral ranges, quotient signals are derived from intensity values of the images of the image sequence for at least one capillary vessel region of the fundus, which quotient signals represent a capillary vessel response of the vessels of the at least one capillary vessel region to the stimulation, and an absolute or percentage maximum change is determined from the quotient signals or/and a quotient signal averaged from the quotient signals and is used as an evaluation criterion for the neurovascular coupling.

In the second method, advantageously, diameter signals are derived from the images of the image sequence for at least one vessel section of arterial or venous vessels of the fundus, which diameter signals represent an arterial or venous vessel response of the at least one vessel section to the stimulation, and from the diameter signals an averaged diameter signal is formed, the absolute or percentage maximum change of which is determined, which represents an evaluation criterion for the endothelial function.

By forming a quotient from the maximum change of the averaged quotient signal and the maximum change of the averaged diameter signal, an evaluation criterion for an evaluation of the vascular endothelial function is advantageously created which is free from the influence of the neurovascular coupling.

By illuminating the fundus with measuring light of two different spectral ranges, the images can be assigned to two color channels, each determined by one of the spectral ranges, and the signal formed can be a quotient signal derived from the intensity values of the two color channels.

Advantageously, the imaging method is based on optical coherence tomography and the images are OCT images.

The flickering light preferably has a spectral range different from the measuring light, allowing the measuring light and the flickering light to be adjusted independently of each other.

Advantageously, the maximum change of the quotient signal and/or of the diameter signal is presented in color-coded form in a mapping image assigned to the at least one capillary vessel region and/or the at least one vessel section.

With respect to a device for examining the neurovascular coupling at the eye of a patient, the object is achieved by a first device comprising:

an imaging system for generating an image sequence of images of the fundus of the eye, which images depict intensities of the structures characterizing the fundus, the capillary density, the blood velocity, the blood flow or the blood volume of the vessels, with an illumination unit for generating flickering light with which at least a section of the fundus is stimulated, a data and image processing unit designed to select capillary vessel regions and vessel sections of arterial and venous vessels from the images of the image sequence, a unit for deriving signals assigned to the selected capillary vessel regions and the selected vessel sections, a signal analysis unit and a result and presentation unit.

With respect to a device for examining the neurovascular coupling at the eye of a patient, the object is also achieved by a second device comprising:

an imaging system for generating an image sequence of images of the fundus of the eye, with an illumination unit designed to generate a measuring light, with at least two spectral ranges for illumination, and to generate a flickering light for stimulating the fundus, a data and image processing unit designed to select capillary vessel regions and vessel sections of arterial and venous vessels in the images of the image sequence, a unit for deriving quotient signals assigned to the selected capillary vessel regions, a unit for deriving diameter signals assigned to the selected vessel sections, a signal analysis unit and a result and presentation unit, wherein the illumination unit is formed by a structured arrangement of adaptively controllable LEDs as an illumination structure with at least three different spectral ranges, the geometry and dimension of which can be changed over time, whereby selected capillary vessel regions and/or selected vessel sections can be adaptively illuminated and stimulated.

The imaging system is advantageously embodied as a fundus camera with a digital image sensor, an optical coherence tomograph (OCT), a scanning imaging system or a system with adaptive optics.

Advantageously, the LEDs of two spectral ranges generate the measuring light and, in an independently controllable manner, the LEDs of the third spectral range generate the flickering light.

Further, the spectral ranges of the LEDs generating the measuring light are preferably green and red, and the spectral range of the LEDs generating the flickering light is blue.

The digital image sensor is advantageously a color image sensor with at least two color channels.

As an alternative, it is advantageous for the digital image sensor to be a monochromatic image sensor, the spectral ranges of the measuring light lying within and the spectral range of the flickering light lying outside the spectral sensitivity of the digital image sensor.

BRIEF DESCRIPTION OF THE DRAWINGS

The invention will be explained in more detail below with reference to exemplary embodiments and drawings.

In the drawings.

DETAILED DESCRIPTION OF THE PREFERRED EMBODIMENTS

Figure 1:
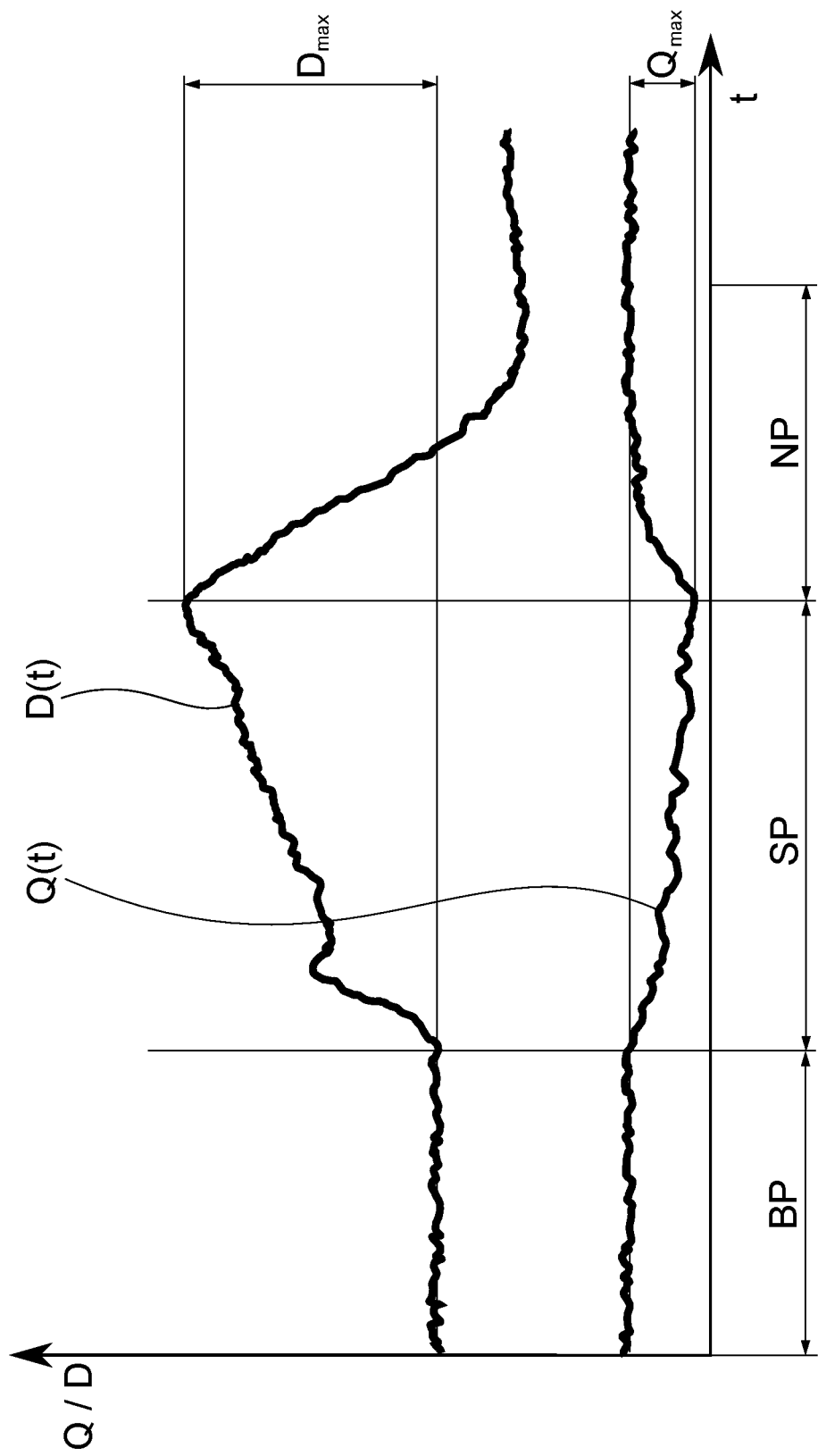
FIG. 1 shows the time course of a quotient signal and a diameter signal over the duration of the method.

In a method for examining neurovascular coupling at the eye A, an imaging method is used to record an image sequence of images of the fundus of the eye, preferably over a baseline phase BP, a stimulation phase SP in which the fundus is stimulated with a flickering light, and a posterior phase NP, see FIG. 1.

A signal is derived from the image sequence for at least one capillary vessel region KGB, which represents a capillary vessel response (signal of a measured variable) of the capillary vessels to the stimulation of the retina and whose maximum change during the stimulation phase SP represents an evaluation criterion (biomarker) for NVC. Basically, such a capillary vessel response (vascular signal) can be the changes in capillary blood flow or capillary blood velocity, in capillary vessel diameter or capillary blood volume in the retina or on the optic nerve head during the stimulation phase SP.

It is irrelevant by which imaging method the at least one image sequence is formed or by which measurement parameters the NVC is determined.

The image sequence of images can be generated, for example, by optical coherence tomography OCT, by a scanning method or by other optical imaging methods.

Advantageously, and as described in the following exemplary embodiment of a method, the change of the capillary blood volume or of the vessel diameter of the capillary vessels, respectively, which results in a change in the proportion of the measuring light reflected at the retinal capillary vessel regions KGB or the papillary capillary vessel regions KGB (on the papilla), is detected by a standardized intensity signal (quotient signal $Q(t,x,y)$), which is used as a capillary vessel response for the examination of NVC.

Advantageously, the method integrates the examination of endothelial function in the large retinal vessels and/or venous retinal vessels.

Step 0:

At the beginning of the method, an examination program menu for different examinations relating to different medical questions is presented to the examiner. The selection of examination parameters serves to adjust the parameters of the measuring light and the parameters of the flickering light.

The examiner can choose between adjusting 0-1: freely selected parameters (free parameter selection), 0-2: comparative parameters (comparative mode), and 0-3: repetition parameters (repeat mode), as described in the following process steps:

Step 0-1: Free Parameter Selection

For research questions, free parameter selection is often useful. The following parameters are preferably presented to the examiner for automatic pre-adjustment, and after selection the set of parameters is stored as a new program for comparative and repeat examinations under a name to be assigned by the examiner.

Step 0-1-1: Adjustment of the Measuring Light (Measuring Light Parameters)

Definition of two spectral ranges of the measuring light, preferably green and red, if a normalized intensity signal (quotient signal $Q(t,x,y)$) is to be derived from the image sequences, and definition of a spectral range, e.g. green, if a non-standardized intensity signal is to be derived from the image sequences Definition of the radiation intensity of the measuring light (manually or automatically re-adjustable, controlled by image brightness)

Definition of the time response during the stimulation phase SP. If the measuring light and the flickering light have the same spectral range (e.g. green), e.g. at an imaging frequency of 25 Hz, the measuring light is deactivated during the stimulation phase SP at every 2nd image with a predetermined modulation depth to realize a flicker stimulation frequency of 12.5 Hz. Advantageously, different spectral ranges are defined for the measuring light and the flickering light. Thus, blue is also preferred as additional measuring light in combination with red.

Step 0-1-2: Adjustment of the Flickering Light (Flickering Light Parameters)

Adjustment to luminance flicker or color flicker

For luminance flicker, the defined spectral range of the flickering light is modulated only in accordance with the other flicker parameters. In the case of color flicker, the flickering light only changes the spectral range with the flicker frequency, which means mutual switching of the different-color LEDs.

The adjustment of the spectral ranges of the color LEDs is performed in accordance with the flicker type, e. g. in the case of color flicker, the flickering light is set to change from a blue LED to a green LED.

Adjustment of the modulation of the flickering light

In the present example, the examiner may define the form of stimulation for each half-period of the flickering light using the following parameters:

intensity maximum intensity minimum modulation depth intensity increase intensity decrease duration of the intensity maximum wave-shaped or step-shaped modulation For the exemplary embodiment, where the green and red spectral ranges were selected as measuring light, a color that is not in the spectral range of the measuring light, e.g. blue, is defined for the flickering light. This allows the flicker frequency to be defined independently of the imaging frequency.

Step 0-1-3: Adjustment of the Examination Phases (Phase Parameters)

This involves the adjustment of the duration of the examination phases, i.e. the baseline phase BP, the stimulation phase SP and the posterior phase NP.

Step 0-1-4:

All freely adjusted parameters are combined in a set of parameters and stored with an examination name and presented upon renewed selection of the examination program.

Step 0-2: Comparative Mode (Ensures the Same Examination Conditions for Different Eyes a for the Same Medical Question)

The desired examination program for the medical question is selected from the examination menu and the respective set of parameters for the selected examination program is loaded. The LEDs of a device for performing the method are controlled accordingly via provided control algorithms, thereby adjusting the measuring light and the flickering light to the selected examination program in a variable and adaptive manner.

Step 0-3: Repeat Mode (Ensures the Same Examination Conditions in Follow-Up Sessions for the Same Eye A) with Reference Measurement Locations The eye A already examined previously is selected from a patient-related database, and the parameter sets stored for the last examination carried out are preset.

During adjustment of the device to the eye A, movement correction ensures an exact match, from one session to the next, of the areas of the fundus F captured in the images of the image sequences.

After adjustment of all parameters, the examination procedure begins.

Step 1:

The patient's head is held in place with respect to an imaging system 1 by a head and chin rest. The imaging system 1 is adjusted in such a way to the eye A to be examined that it provides a low-scatter and reflection-free image of the fundus.

Step 2:

At the beginning of the baseline phase BP the imaging system 1 starts to record an image sequence of images. When using a color sensor as the digital image sensor 2, images are synchronously generated over two color channels when the fundus is illuminated with measuring light of two spectral ranges, for example with green and red measuring light. In the following, they will be understood to be images to which two color channels are assigned. Alternatively, a monochromatic image sensor can be used as the digital image sensor 2. With a temporally changing illumination synchronous to the image sequence, for example with red and green measuring light, images are also generated which are alternately assigned to a pseudo green color channel and a pseudo red color channel and are subsequently understood to be pairs of images to which two color channels are assigned. To avoid unwanted stimulation with the measuring light change, the image change and the spectral measuring light change are performed at such a high frequency that a possible stimulation effect is negligible. The flickering light remains deactivated during the baseline phase BP.

Step 3:

The images of the image sequences are corrected for eye movements. Capillary vessel regions KGB are selected in the images of the fundus and, preferably simultaneously, quotient signals $Q(t,x,y)$ are formed from the intensity values of the red and green color channels of the images, starting with the acquisition of the images, and are stored so as to be respectively assigned to one of the selected capillary vessel regions KGB.

The values of the parameters of the quotient signals Q(t,x,y) over the duration of the baseline phase BP provide baseline values from which a mean baseline value is determined.

Step 4:

Advantageously, diameter signals D(t,x,y) are derived simultaneously from the intensity values of the green color channels of the images of the image sequence. For this purpose, the vessel diameter along the selected vessel sections GA is determined segment by segment, each section being assigned to a measurement location M(x,y), is stored in a location-corrected manner and is assigned to a synchronization signal or the individual images of the image sequence, respectively. Based on the diameters determined, diameter signals D(t,x,y) are formed for each vascular segment. The values of the parameters of the diameter signals D(t,x,y) over the duration of the baseline phase BP provide baseline values from which a mean baseline value is determined.

Step 5:

The baseline phase BP is automatically followed by the stimulation phase SP with the stimulation time and the set of parameters transferred for the stimulation with flickering light. The aforementioned vascular signals, i.e. the quotient signals Q(t,x,y) and the diameter signals D(t,x,y), are further derived from the image sequences during the stimulation phase SP. When using a monochromatic image sensor as the digital image sensor 2, the measuring light of both spectral ranges is deactivated synchronously to the image sequence in the bright phases of the blue flickering light, while in the dark phase of the flickering light the measuring light is switched on and the images and consequently the vascular signals are generated. If the monochromatic image sensor is not sensitive to the blue flickering light, the recording of the images and the derivation of the vascular signals can also be performed during the bright phase of the flickering light. The flicker induced changes of the quotient signals Q(t,x,y) and the diameter signals D(t,x,y) are evaluated in terms of their scattering and dilation. An averaged diameter signal D(t) is formed separately for the individual quotient signals Q(t,x,y) or for an averaged quotient signal Q(t) or for the individual diameter signals D(t,x,y) or for the arterial vessel sections GA and the venous vessel sections GA. The averaged quotient signal Q(t) is used to determine $Q_{max}$ and the averaged diameter signals D(t) are used to determine $D_{max}$ as the maximum change of the signal.

Step 6:

After terminating the stimulation phase SP, the posterior phase NP of the examination begins, the flickering light is deactivated and the continuous measurements are continued until the posterior phase NP is terminated. The stimulation phase SP and the posterior phase NP may be repeated alternately several times, preferably three times, for averaging the signals.

Step 7:

The signals Q(t,x,y) and D(t,x,y) are averaged over the selected KGB and GA, recorded and output as a measurement report with the derived maximum values of the signal changes.

An exemplary embodiment of a device suitable for carrying out the method will be described below.

Figure 2:
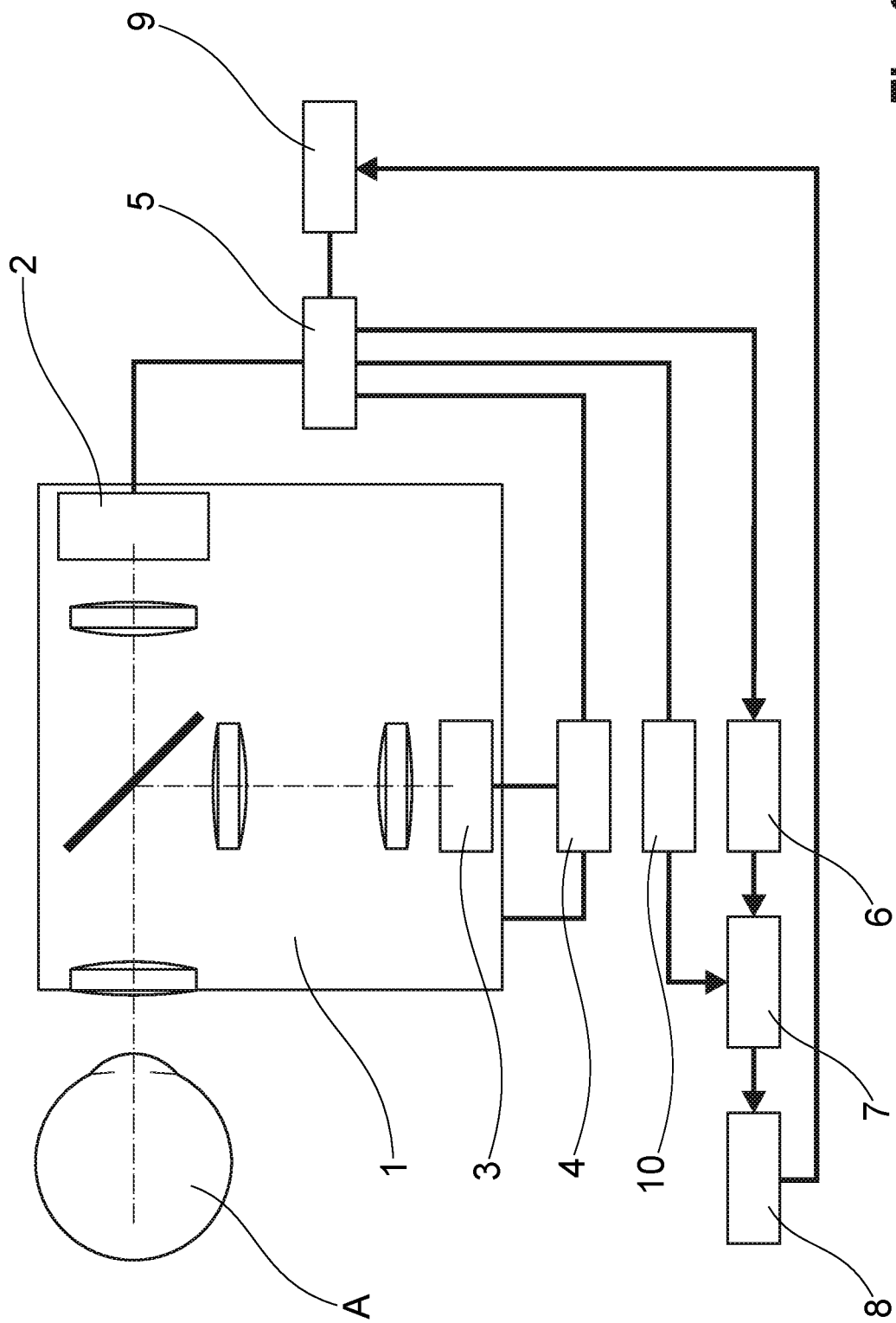
FIG. 2 shows a block diagram of a device suitable for performing the method.

As shown in a block diagram in FIG. 2, such a device contains an imaging system 1, in this case a modified retinal camera, with a digital image sensor 2 and an illumination unit 3 for generating a measuring light and a flickering light, a control unit 4, a data and image processing unit 5, a unit for deriving diameter signals 6, a signal analysis unit 7, a result and presentation unit 8, an input and output unit 9 and a unit for deriving quotient signals 10.

The illumination unit 3 is arranged in an illumination beam path of the retinal camera in a plane conjugate to the pupil, i.e. it is imaged into the pupil of the eye A. The fundus of the eye A is sharply imaged on a reception surface of the digital image sensor 2.

The illumination unit 3 is a preferably adaptive, structured, ring-shaped arrangement of small light sources, e.g. LEDs with three different spectral characteristics, preferably in the blue, green and red spectral ranges. The LEDs are controlled via the control unit 4 such that the LED light intensities of the different-color LEDs are modeled separately and independently of each other. The modulation of the LED light is intended to enable both the adjustment of the radiation intensity of light as the measuring light and the adjustment of flickering light by alternating between high and low radiation intensity, with adjustable parameters of the frequency, the modulation depth and the alternating light shape (e.g. wave-shaped to step-shaped, symmetrical or asymmetrical change between bright and dark phases). Advantageously, the luminous structure formed by the active (luminous) LEDs can be adaptively adjusted in its geometry and dimension, e.g. the width and diameter of an active, formed luminous ring. By means of the adaptivity of the temporally and geometrically active LED structure as e.g. a temporally changing, thin or wide ring or half ring or dot, the ring-shaped LED arrangement can be inserted in the illumination-side aperture stop to reduce scattered light or reflection light (especially on the vessels). This also allows the dynamic vessel analysis to be switched very quickly to the mode of non-mydriatic static vessel analysis, and vice versa. At the same time, said adaptivity also allows the fundus to be focused via the principle of Scheiner apertures. A structural change rotating during the examination can also be used to capture image sequences with different illumination geometries.

The digital image sensor 2 may be a color sensor that, when illuminated with green and red measuring light, synchronously generates images which are assigned to a green and a red color channel. The two synchronous images are understood to be one image to which two color channels are assigned.

Advantageously, a monochromatic image sensor is used as the digital image sensor 2, which is preferably only sensitive to the two spectral ranges of the measuring light, but not to the spectral range of the flickering light. When the fundus is illuminated synchronously to the image sequence, image by image, alternately with red and green measuring light, the images are assigned alternately to a pseudo green and a pseudo red color channel. Two successively recorded images are understood to be one image to which two color channels are assigned. The imaging frequency is set so high that the color change of the measuring light does not result in a stimulation effect.

Advantageously, the two pseudocolor channels of the monochromatic image sensor have a higher sensitivity and the monochromatic image sensor has a higher resolution than the color image sensor.

Both the use of a color image sensor and the use of a monochromatic image sensor as a digital image sensor allow a free choice of spectral ranges for the measuring light and the flickering light, which only have to be different.

The adaptive control unit 4 is connected to the data and image processing unit 5, which is in turn connected to the digital image sensor 2. It controls the individual LEDs of the illumination unit 3 separately from each other and with different radiation intensities, but—at least when the LEDs emit the measuring light—synchronized to the image sequence. The frequency of the flickering light (change between bright and dark) is controlled by a synchronization signal which is generated by the digital image sensor 2 and is transmitted to the control unit 4. The synchronization signal is used to synchronize the signals formed during the process steps with the image sequence recorded by the digital image sensor 2. It does not matter whether the synchronization signal is given by the digital image sensor 2 or by the data and image processing unit 5 which also controls the recording of the images of the image sequence.

In contrast to the monochromatic image sensor, the color image sensor records images of the fundus at an imaging frequency of preferably 25 Hz, which preferably results in a flicker frequency of 12.5 Hz. However, according to the invention, any other imaging frequency synchronized with a flicker frequency may be used for the device and the method. The imaging frequency and the flicker frequency do not even have to be synchronized with each other, if there is no overlap of the spectral ranges of the measuring light and the flickering light.

Figure 3:
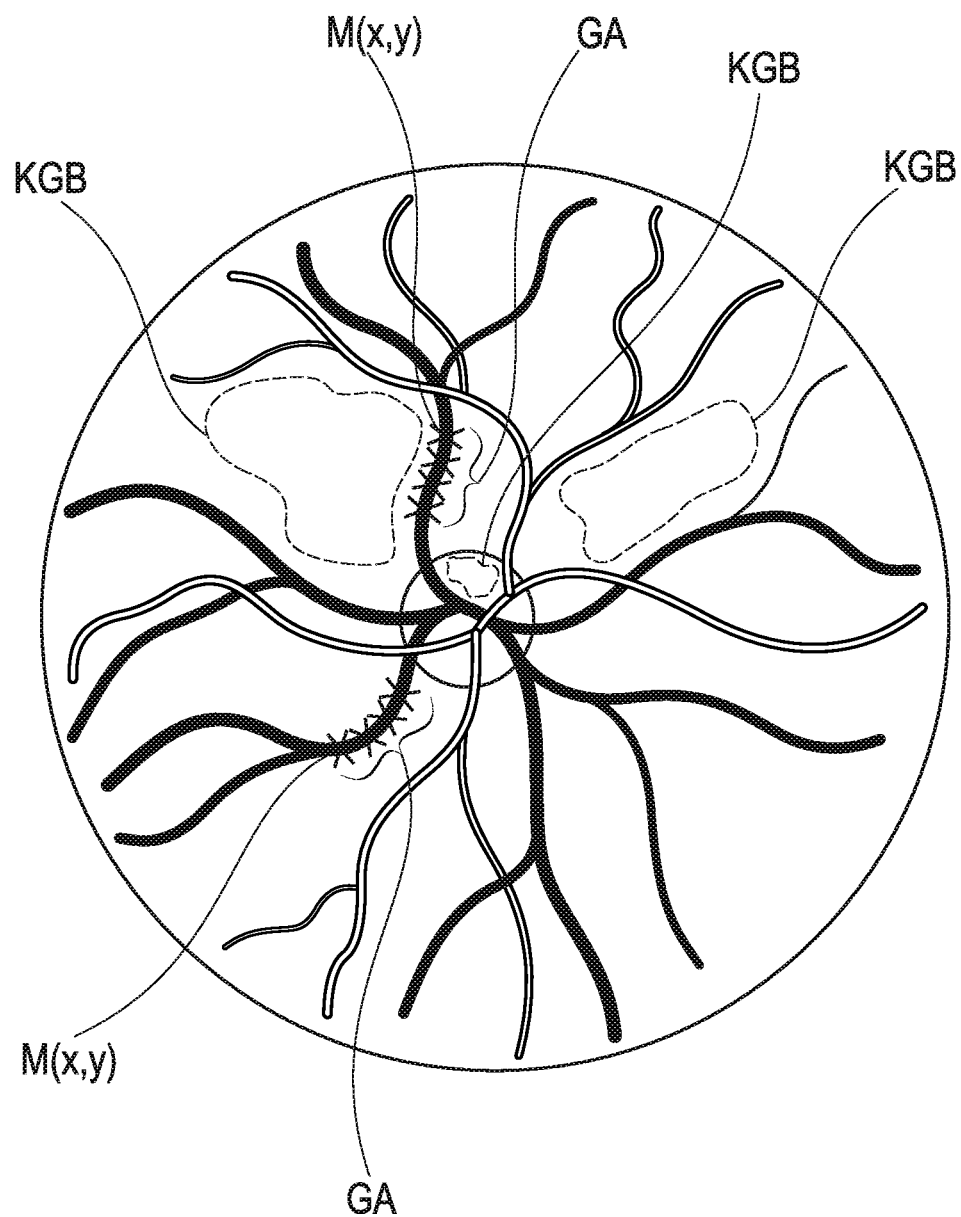
FIG. 3 shows an image of the fundus, providing examples of capillary vessel regions, including one on the optic nerve head, as well as measurement locations and vessel sections.

The data and image processing unit 5 connected to the digital image sensor 2 receives the image sequence. The examiner uses the data and image processing unit 5 and the input and output unit 9 to select the capillary vessel regions KGB in the retina or on the optic nerve head in the images, see FIG. 3, and assigns a measurement location M(x,y) to each of them. A measurement location M(x,y) can be defined by an image point or an image area and thus a pixel or a pixel group of the digital image sensor 2. The measuring location M(x,y) can be the area center of the KGB or another selected point in the KGB. In addition, larger venous and arterial vessel sections GA are selected in the images, to which are assigned, segment by segment, measuring locations M(x,y) and thus image points or individual pixels, which here preferably represent the center of the respective vascular segment, or image areas, here the vascular segments, or a pixel group on the digital image sensor 2. The selected KGBs are advantageously located between the selected vessel sections GA.

The coordinates of the measuring locations M(x,y) assigned to the KGBs and the green and red intensity values generated at the measuring locations M(x,y) by the green and red measuring light are transferred to the unit for deriving quotient signals 10.

The coordinates of the vascular segments or the assigned measuring locations M(x,y) and the intensity values generated by the green measuring light are transmitted to the unit for deriving diameter signals 6.

The unit for deriving quotient signals 10 forms, online from image to image and as a function of time, quotients from the green and red intensity values of the images for all measurement locations M(x,y) of the KGBs and transmits these values as quotient signals Q(t,x,y) to the signal analysis unit 7.

The unit for deriving diameter signals 6 only needs to be present if the device is advantageously used to examine vascular endothelial function in addition to neurovascular coupling. The unit for deriving diameter signals 6 determines the diameter online, via image processing of the green color signals segment by segment and image by image, forms diameter signals D(t,x,y) as a function of time and place and transmits them to the signal analysis unit 7. There the diameter signals D(t,x,y) of the vascular segments are combined to form diameter signals D(t,x,y) for entire vascular segments GA or diameter signals D(t) averaged over all arterial or venous vessel sections, which are graphically displayed and output to the examiner via the result and presentation unit 8. In the signal analysis unit 7, typical parameters of the vessels, describing the endothelial function, such as, for example, the maximum dilation in the stimulation phase SP, are also computed and output via the result and presentation unit 8 and the input and output unit 9. The result and presentation unit 8 additionally serves to generate mapping images.

The signal analysis unit 7 determines, as parameters of the signals, the maximum change in vessel diameter, equal to the maximum dilation $D_{max}$, from the diameter signals D(t,x,y) for the vascular segments or vessel sections GA or from the averaged diameter signals D(t) and the maximum change $Q_{max}$ from the quotient signals Q(t,x,y) for the capillary vessel sections KGB. The maximum dilation $D_{max}$ describes the endothelial function and the maximum change $Q_{max}$ describes the NVC. The parameters are transmitted to the result and presentation unit 8, entered in the correct location (movement-corrected) in a result image (mapping image) and output as an examination result.

The examination results for NVC and endothelial function can be medically evaluated separately, but advantageously in conjunction.

The examination of NVC on the basis of quotient signals Q(t,x,y) has the advantage that the blood volume of the KGBs is measured using spectrally normalized intensity values. Since these intensity values are independent of illumination, a different illumination of the measurement locations M(x,y) due to eye movements has at most an insignificant influence on the parameter describing NVC.

For simplification, instead of the quotient signal Q(t,x,y) formed from the intensity values of two spectral ranges, an intensity signal of only one spectral range, e.g. the green spectral range, can also be formed to examine NVC. In this case, however, movement-dependent changes in illumination have to be accepted or other possibilities have to be found to eliminate them. For example, the intensity signal could be normalized to measurement locations on the fundus or on the optic nerve head that are not within the effective area of flicker stimulation.

A further exemplary embodiment of a method and device according to the invention is obtained if instead of a modified fundus camera, as described above, a laser scanner is used as the imaging system 1, with laser beams whose wavelengths are matched to the spectral ranges of the measuring light and flickering light already described above. The method and the device are embodied in the same way as described above.

The use of adaptive optics as the imaging system 1 or as components of the imaging system 1 is also covered by a device according to the invention. In these cases both quotient signals Q(t,x,y) and diameter signals D(t,x,y) can be formed as described above.

Further exemplary embodiments result from the use of imaging systems 1 based on optical coherence tomography (OCT). Signals are derived from the images, in this case so-called OCT images, which describe both the local vessel diameters of larger vessels and/or the local blood volume or the local perfusion of the capillaries. Such signals can be derived from local blood flow, local blood or cell velocity or capillary density and also represent the vascular reaction to flickering light from different points of view. An example of an imaging system 1 based on optical coherence tomography is an angiograph (OCT-A), in whose OCT images the signals are represented by the moving blood cell density or the capillaries perfused with blood cells.

Figure 4:
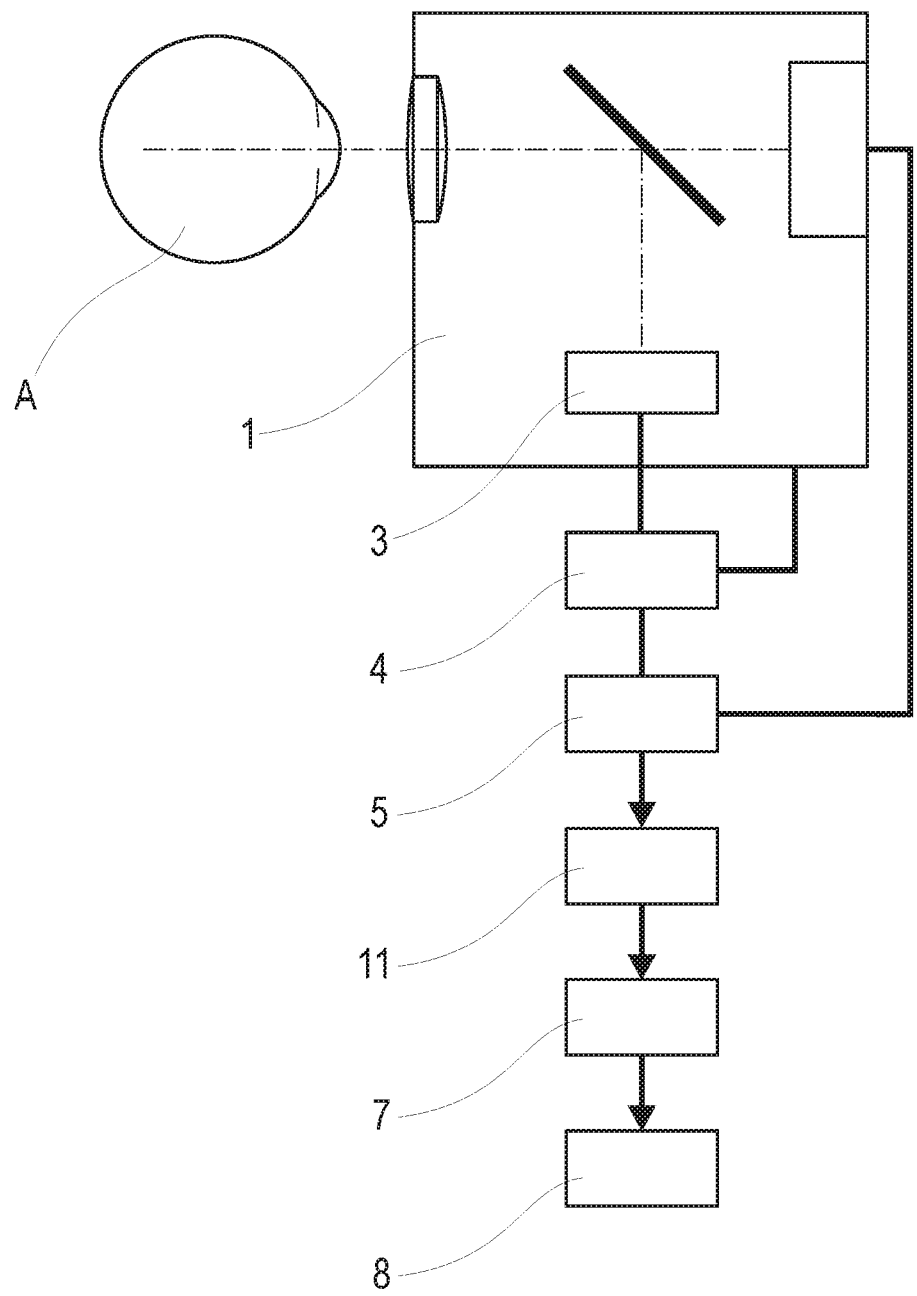
FIG. 4 shows a block diagram of a further device suitable for performing the method.

As shown in FIG. 4, the device for examining the neurovascular coupling at the eye A of a patient can basically comprise any imaging system 1 designed to generate an image sequence of images of the fundus of the eye A. The imaging system 1 only needs to be designed to produce images in which intensities of the structures characterizing the fundus, capillary density, blood velocity, blood flow or blood volume of the vessels are depicted. In addition, an illumination unit 3 is present for the generation of flickering light, by which at least one section of the fundus can be stimulated. Moreover, the device must comprise a data and image processing unit 5 designed to select capillary vessel regions KGB and vessel sections GA of arterial and venous vessels from the images of the image sequence, a unit for deriving signals 11 assigned to the selected capillary vessel regions (KGB) and the selected vessel sections GA, a signal analysis unit 7 and a result and presentation unit 8.

LIST OF REFERENCE NUMERALS

D(t,x,y) diameter signal (as a function of time and location x, y)
D(t) averaged diameter signal
$D_{max}$ maximum change of the diameter signal D(t,x,y)
Q(t,x,y) quotient signal (as a function of time and location x, y)
Q(t) averaged quotient signal
$Q_{max}$ maximum change of the quotient signal Q(t,x,y)
M(x,y) measurement location
BP baseline phase
SP stimulation phase
NP posterior phase
GA vessel section
KGB capillary vessel region
A eye
1 imaging system
2 digital image sensor
3 illumination unit
4 control unit
5 data and image processing unit
6 unit for deriving diameter signals
7 signal analysis unit
8 result and presentation unit
9 input and output unit
10 unit for deriving quotient signals
11 unit for deriving signals

What is claimed is:

1. A method for examining neurovascular coupling at an eye (A) of a patient, the method comprising:
generating and recording an image sequence of images of a fundus of the eye (A) by an imaging method while stimulating the fundus with a flickering light;
deriving signals from the images of the image sequence for at least one capillary vessel region (KGB) of the fundus, the signals representing capillary vessel responses of capillaries of the capillary vessel region (KGB) to the stimulating with the flickering light, wherein the signals' maximum absolute or percentage change is determined and used as an evaluation criterion for the neurovascular coupling.

2. The method according to claim 1, wherein the signals are derived from the images of the image sequence for at least one vessel section (GA) of arterial or venous vessels of the fundus, the signals representing arterial and/or venous vessel responses to the stimulating, wherein the signals' maximum absolute or percentage change is determined and used as an evaluation criterion for an endothelial function.

3. The method according to claim 2, further comprising using the maximum absolute or the percentage change in the capillary vessel responses as a reference value for the maximum absolute or the percentage change in the arterial and/or venous vessel responses, and calculating a quotient representing an evaluation criterion for evaluating the vascular endothelial function free from an influence of the neurovascular coupling.

4. The method according to claim 1, wherein the signals representing the vessel responses represent intensities, vessel diameters, blood volume values, quotient signals (Q(t,x,y)) from different spectral ranges, blood flow values and blood velocity values of the capillaries or larger arterial or venous vessels.

5. The method according to claim 1, further comprising recording the image sequence of images of the fundus of the eye (A) over a baseline phase (BP), a stimulation phase (SP) in which the fundus is stimulated with the flickering light, and a posterior phase (NP).

6. A method for examining neurovascular coupling at an eye (A) of a patient, the method comprising:
using an imaging method to record an image sequence of images of the fundus of the eye (A) over a baseline phase (BP), a stimulation phase (SP) in which the fundus is stimulated with a flickering light, and a posterior phase (NP);
illuminating the fundus with measuring light of two different spectral ranges, deriving quotient signals (Q(t,x,y)) from intensity values of the images of the image sequence for at least one capillary vessel region (KGB) of the fundus, the quotient signals representing a capillary vessel response of the vessels of the at least one capillary vessel region (KGB) to the stimulation, and determining an absolute or percentage maximum change ($Q_{max}$) from the quotient signals (Q(t,x,y)) or/and a quotient signal (Q(t)) averaged from the quotient signals (Q(t,x,y)) and using the absolute or percentage maximum change ($Q_{max}$) as an evaluation criterion for the neurovascular coupling.

7. The method according to claim 6, further comprising deriving diameter signals (D(t,x,y)) from the images of the image sequence for at least one vessel section (GA) of arterial or venous vessels of the fundus, which diameter signals represent an arterial or venous vessel response of the at least one vessel section (GA) to stimulation, and forming an averaged diameter signal (D(t)) from the diameter signals (D(t,x,y)), and determining the absolute or percentage maximum change ($D_{max}$) of the averaged diameter signal (D(t)) which represents an evaluation criterion for an endothelial function.

8. The method according to claim 7, further comprising forming a quotient from the maximum change ($Q_{max}$) of the averaged quotient signal (Q(t)) and the maximum change ($D_{max}$) of the averaged diameter signal (D(t)), the quotient representing an evaluation criterion for an evaluation of the vascular endothelial function which is free from an influence of the neurovascular coupling.

9. The method according to claim 6, wherein the imaging method is based on optical coherence tomography and the images are OCT images.

10. The method according to claim 6, wherein
the flickering light has a spectral range different from that of the measuring light and wherein the measuring light of the different spectral ranges and the flickering light can be adjusted independently of each other.

11. The method according to claim 8, further comprising presenting the maximum change ($Q_{max}$) and/or ($D_{max}$) in a color-coded form in a mapping image assigned to the at least one capillary vessel region (KGB) and/or the at least one vessel section (GA).

12. A device for examining neurovascular coupling at an eye (A) of a patient, the device comprising:
   an imaging system for generating an image sequence of images of a fundus of the eye (A), the images depicting intensities of structures characterizing the fundus, capillary density, a blood velocity, a blood flow or a blood volume of vessels;
   an illumination unit for generating flickering light with which at least a section of the fundus is stimulated;
   a data and image processing unit for selecting capillary vessel regions (KGB) and vessel sections (GA) of arterial and venous vessels from the images of the image sequence;
   a unit for deriving signals assigned to selected capillary vessel regions (KGB) and the selected vessel sections (GA);
   a signal analysis unit; and
   a result and presentation unit.

13. A device for examining neurovascular coupling at the eye (A) of a patient, said device comprising:
   an imaging system for generating an image sequence of images of a fundus of the eye (A);
   an illumination unit for generating a measuring light with at least two spectral ranges for illumination and for generating a flickering light for stimulating the fundus;
   a data and image processing unit for selecting capillary vessel regions (KGB) and vessel sections (GA) of arterial and venous vessels in the images of the image sequence;
   a unit for deriving quotient signals assigned to selected capillary vessel regions (KGB);
   a unit for deriving diameter signals assigned to selected vessel sections (GA); and
   a signal analysis unit and a result and presentation unit (8);
   wherein the illumination unit is formed by a structured arrangement of adaptively controllable LEDs having geometry and dimension changeable over time, the adaptively controllable LED having at least three different spectral ranges, whereby the selected capillary vessel regions (KGB) and/or the selected vessel sections (GA) can be adaptively illuminated and stimulated.

14. The device according to claim 13, wherein
   the measuring light can be generated by controlling the controllable LEDs of two spectral ranges and the flickering light can be generated by controlling the controllable LEDs of a third spectral range, whereby the measuring light and the flickering light can be generated independently of each other.

15. The device according to claim 13, wherein the imaging system is designed as a fundus camera comprising a digital image sensor.

16. The device according to claim 12, wherein the imaging system is an optical coherence tomograph (OCT) or a scanning imaging system or a system with adaptive optics.

17. The device according to claim 14, wherein
   The two spectral ranges of the controllable LEDs generating the measuring light are green and red and the third spectral range of the LEDs generating the flickering light is blue.

18. The device according to claim 15, wherein
   the digital image sensor is a monochromatic image sensor, and wherein the at least two spectral ranges of the measuring light lying within a spectral sensitivity of the digital image sensor and a spectral range of the flickering light lying outside the spectral sensitivity of the digital image sensor.

* * * * *